US011357768B2

(12) United States Patent
Febbraio et al.

(10) Patent No.: US 11,357,768 B2
(45) Date of Patent: Jun. 14, 2022

(54) METHODS FOR TREATING NASH AND FOR PREVENTING NASH-INDUCED HCC

(71) Applicant: N-GENE RESEARCH LABORATORIES, INC., New York, NY (US)

(72) Inventors: Mark Anthony Febbraio, New South Wales (AU); Jozsef Mandl, Budapest (HU)

(73) Assignee: N-GENE RESEARCH LABORATORIES, INC., New York, NY (US)

(*) Notice: Subject to any disclaimer, the term of this patent is extended or adjusted under 35 U.S.C. 154(b) by 0 days.

(21) Appl. No.: 16/617,655

(22) PCT Filed: Jun. 8, 2018

(86) PCT No.: PCT/IB2018/054155
§ 371 (c)(1),
(2) Date: Nov. 27, 2019

(87) PCT Pub. No.: WO2018/225026
PCT Pub. Date: Dec. 13, 2018

(65) Prior Publication Data
US 2020/0179363 A1    Jun. 11, 2020

Related U.S. Application Data

(60) Provisional application No. 62/516,681, filed on Jun. 8, 2017.

(51) Int. Cl.
*A61K 31/445* (2006.01)
*A61K 31/4545* (2006.01)
*A61P 1/16* (2006.01)
*A61K 45/06* (2006.01)

(52) U.S. Cl.
CPC ............ *A61K 31/4545* (2013.01); *A61P 1/16* (2018.01); *A61K 45/06* (2013.01)

(58) Field of Classification Search
CPC ....... A61K 31/4545; A61K 38/02; A61P 1/16; A61P 3/00
USPC .................................................. 514/340, 1.1
See application file for complete search history.

(56) References Cited

FOREIGN PATENT DOCUMENTS

| WO | 97/13504 A1 | 4/1997 |
| WO | 2005/123049 A2 | 12/2005 |
| WO | 2013/003593 A1 | 1/2013 |

(Continued)

OTHER PUBLICATIONS

Racz et al. "BGP-15—a novel poly(ADP-ribose) polymerase inhibitor—protect against nephrotoxicity of cisplatin without compromising its antitumor activity" Biochemical Pharmacology, 2002, vol. 63, pp. 1099-1111 (Year: 2002).*

(Continued)

*Primary Examiner* — Shengjun Wang
(74) *Attorney, Agent, or Firm* — Nixon & Vanderhye

(57) ABSTRACT

Disclosed are methods of treating non-alcoholic steatohepatitis (NASH) and methods of preventing NASH-induced hepatocellular carcinoma (HCC), such methods including administering O-(3-piperidino-2-hydroxy-1-propyl)-nicotinic amidoxime (BGP15), alone or in combination with a inhibitor of the interleukin-6 receptor transsignaling response, particularly gp130Fc.

1 Claim, 3 Drawing Sheets

(56) References Cited

FOREIGN PATENT DOCUMENTS

WO 2013/024311 A1 2/2013

OTHER PUBLICATIONS

Mukhopadhyay et al. "PARP inhibition protects against alcoholic and non-alcoholic steatohepatitis," J. Hepatology, 2017 vol. 66,2002 pp. 589-600. (Year: 2016).*

Takaki et al. "Multiple Hits, including oxidative stress, as pathogenesis and treatment target in non-alcoholic steatohepatitis (NASH)" Int. J. Mol. Sci. 2013, vol. 14, pp. 20704-20728. (Year: 2013).*

Cuadrado et al. "Non-alcoholic steatohepatitis (NASH) and hepatocellular carcinoma," Obesity Surgery, 2005, vol. 15, pp. 442-446 (Year: 2005).*

International Search Report, dated Sep. 12, 2018, from corresponding PCT application No. PCT/IB2018/054155.

Written Opinion, dated Sep. 12, 2018, from corresponding PCT application No. PCT/IB2018/054155.

Tamas et al.; Inflience of BGP-15, a Nicotinic Amidoxime Derivative, on the Vascularization and Growth of Murine Hepatoma Xenografts; Anticancer Research; Mar. 2006; pp. 1023-1028; vol. 26, No. 2A.

Utzschneider et al.; Review: The Role of Insulin Resistance in Nonalcoholic Fatty Liver Disease; The Journal of Clinical Endocrinology & Metabolism; Dec. 1, 2001; pp. 4753-4761; vol. 91, No. 12.

Literati-Nagy et al.; Improvement of Insulin Sensitivity by a Novel Drug, BGP-15, in Insulin-resistant Patients: A Proof of Concept Randomized Double-blind Clinical Trial; Hormone and Metabolic Research; May 2009; pp. 374-380; vol. 41, No. 5.

Bardos et al.; BGP-15, a hydroximic acid derivative, protects against cisplatinor taxol-induced peripheral neuropathy in rats;Toxicology and Applied Pharmacology; Mar. 6, 2003; pp. 9-16; vol. 190.

Cohen et al.; Human Fatty Liver Disease: Old Questions and New Insights; Science; Jun. 24, 2011; pp. 1519-1523; vol. 332.

El-Serag et al.; Epidemiology of Hepatocellular Carcinoma in the United States: Where Are We? Where Do We Go?; Hepatology; Nov. 2014; pp. 1767-1775; vol. 60.

El-Serag; Hepatocellular Carcinoma; The New England Journal of Medicine; Sep. 22, 2001; pp. 1118-1127; vol. 365.

Eroglu et al.; Therapeutic Inducers of the HSP70/HSP110 Protect Mice Against Traumatic Brain Injury; Journal of Neurochemistry; Sep. 2014; pp. 626-641; vol. 130, No. 5.

Farkas et al.; Reduction of acute photodamage in skin by topical application of a novel PARP inhibitor; Biochemical Pharmacology; Nov. 29, 2001; pp. 921-932; vol. 63; Elsevier Science Inc.

Gehrig et al.; Hsp72 preserves muscle function and slows progression of severe muscular dystrophy; Nature; Apr. 19, 2012; pp. 394-398; vol. 484; McMillan Publishers Limited.; London.

Kraakman et al.; Blocking IL-6 trans-Signaling Prevents High-Fat Diet-Induced Adipose Tissue Macrophage Recruitment but Does Not Improve Insulin Resistance; Cell Metabolism; Mar. 3, 2015; pp. 403-416; vol. 21; Elsevier Inc.

Lazo et al.; Prevalence of Nonalcoholic Fatty Liver Disease in the United States: The Third National Health and Nutrition Examination Survey, 1988-1994; American Journal of Epidemiology; May 23, 2013; pp. 38-45; vol. 178, No. 1; Am J Epidemiol.

Maurel et al.; Endoplasmic Reticulum Stress: At the Crossroads of Inflammation and Metabolism in Hepatocellular Carcinoma Development; Cancer Cell; Sep. 8, 2014; pp. 301-303; vol. 26; Elsevier Inc.

Nagy et al.; BGP-15 inhibits caspase-independent programmed cell death in acetaminophen-induced liver injury; Toxicology and Applied Pharmacology; Feb. 15, 2010; pp. 96-103; vol. 243, vol. 1; Elsevier Inc.

Nakagawa et al.; ER stress cooperates with hypernutrition to trigger TNFdependent spontaneous HCC development; Cancer Cell; Sep. 8, 2014; pp. 331-343; vol. 26, No. 3.

Sapra et al.; The small-molecule BGP-15 protects against heart failure and atrial fibrillation in mice; Nature Communications; Dec. 9, 2014; pp. 1-16; vol. 5, No. 5705.

Starley et. al; Nonalcoholic Fatty Liver Disease and Hepatocellular Carcinoma: A Weighty Connection; Hepatology; May 2010; pp. 1820-1831; vol. 51, No. 5.

Szabados et al.; BGP-15, a Nicotinic Amidoxime Derivate Protecting Heart from Ischemia Reperfusion Injury through Modulation of Poly(ADP-ribose) Polymerase; Biochemical Pharmacology; Apr. 2000; pp. 937-945; vol. 59; Elsevier.

Umemura et al.; p62, Upregulated during Preneoplasia, Induces Hepatocellular Carcinogenesis by Maintaining Survival of Stressed HCC-Initiating Cells; Jun. 13, 2016; pp. 935-948; vol. 29; Elsevier Inc.

Wu et al.; Mitochondrial dysfunction in oocytes of obese mothers: transmission to offspring and reversal by pharmacological endoplasmic reticulum stress inhibitors; Development; Feb. 2015; pp. 681-691; vol. 142; The Company of Biologists Ltd.

Clark et al., "The Prevalence and Etiology of Elevated Animotransferase Levels in the United States," The American Journal of Gastroenterology, vol. 98, No. 5, 2003, 960-967.

Halmosi et al., "Effect of Poly(ADP-Ribose) Polymerase Inhibitors on the Ischemia-Reperfusion-Induced Oxidative Cell Damage and Mitochrondrial Metabolism in Langendorff Heart Perfusion System," Molecular Pharmacology 59:1497-1505, 2001.

Nagy et al., "Improvement of Insulin Sensitivity by a Novel Drug Candidate, BGP-15, in Different Animal Studies," Metabolic Syndrome and Related Disorders, vol. 12, No. 2, 2014, pp. 125-131.

* cited by examiner

MuP-UPA HFD + BGP-15

MuP-UPA HFD

METHODS FOR TREATING NASH AND FOR PREVENTING NASH-INDUCED HCC

FIELD OF THE INVENTION

The present invention relates to methods of treating non-alcoholic steatohepatitis (NASH) and to methods of preventing NASH-induced hepatocellular carcinoma (HCC), such methods comprising administering O-(3-piperidino-2-hydroxy-1-propyl)-nicotinic amidoxime (BGP15), alone or in combination with an inhibitor of the interleukin-6 receptor trans signaling response, particularly gp130Fc.

BACKGROUND OF THE INVENTION

Hepatocellular carcinoma (HCC) is one of the most common and fatal cancers world-wide. In developed countries, the past three decades have seen the incidence of HCC treble and become the fastest rising cause of cancer related deaths (El-Serag et al., 2014), initially ascribed to the emergence of hepatitis C virus (HCV). Of note, however, only 50% of the dramatic increase in HCC in developed countries can be linked to HCV. Up to 50% of new HCC are in 'virus absent' patients (El-Serag, 2011) where the etiology of the disease has, until very recently, remained unclear (Starley et al., 2010). Most 'virus absent', HCC patients present with obesity, non alcoholic fatty liver disease (NAFLD) and non alcoholic steatohepatitis (NASH) (Cohen et al., 2011). It is estimated that at least 25% of the population in developed countries has NAFLD (Lazo et al., 2013), with up to 8% of them exhibiting some degree of NASH (Clark et al., 2003).

There is a need for drugs that can treat NASH and prevent NASH patients from developing HCC.

The compound of formula I,

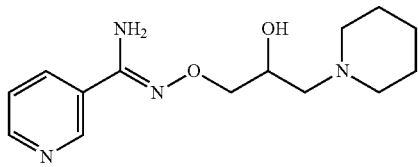

(I)

O-(3-piperidino-2-hydroxy-1-propyl)-nicotinic amidoxime, also known as BGP15, is mostly known in the art for use in the treatment of diabetes (Literáti-Nagy et al., 2014). WO2013024311 and Gehrig et al. (2012) describe the usefulness of BGP15 for treating muscle atrophy, principally by reducing skeletal muscle fibrosis. WO2005123049 describes effect of BGP15 on mitochondrial genesis and its possible use in muscle regeneration. WO9713504 describes the use of BGP15 for neurodegenerative disorders, myopathy and various diseases of mitochondrial origin.

Nagy et al. (2010) describe how BGP15 prevents AIF mitochondria to nucleus translocation and mitochondrial depolarisation in liver cells. WO2005123049 discloses that BGP15 can increase the number of mitochondria in various tissues.

BGP15 is also known for the treatment of acquired muscle myopathy and rhabdomyolysis (WO2013003593), traumatic brain injury (Eroglu et al., 2014), peripheral neuropathy (Bardos et al., 2003) and atrial fibrillation and heart failure (Sapra et al., 2014). Wu et al. (2015) describe how BGP15 increases mtDNA content in oocytes. Halmosi et al. (2001) and Szabados et al. (2000) show how BGP15 protects cardiac cells from reactive oxygen species (ROS) induced inactivation of mitochondria by virtue of its PARP-inhibitory action. Farkas et al. (2002), discusses the effect of BGP15 on skin mitochondria in relation to its anti-PARP activity.

SUMMARY OF THE INVENTION

Figure 1A:
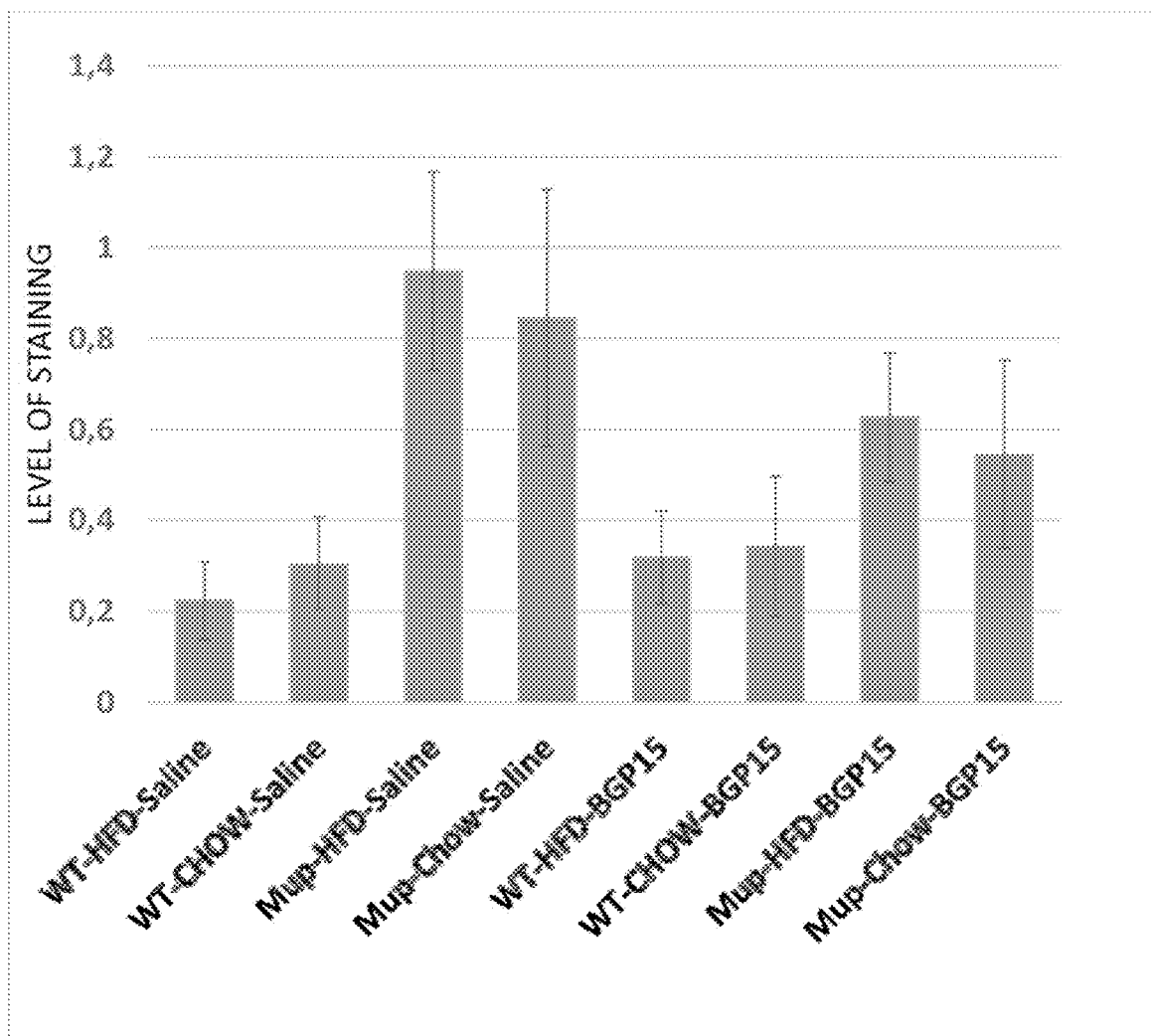
FIG. 1A portrays the level of fibrosis by Sirius red staining of liver cells of wild type mice fed with a Chow or HFD diet, as well as those of MUP-uPA mice under HFD diet treated or untreated with BGP15.

As shown in Nakagawa et al. (2014) and in Maurel et al. (2014), feeding MUP-uPA mice with a High Fat Diet (HFD) leads to these animals developing diseased livers that recapitulate the human features of NASH. Most importantly, these mice exhibit more liver damage, marked liver inflammation and, as a result, display NASH and develop typical steatohepatitic HCC.

Treatment of HFD-fed MUP-uPA mice with BGP15 leads to an amelioration of the condition.

Accordingly, in a first embodiment, there is provided a method to treat NASH in a subject, comprising administering to such subject the compound of formula I, tautomers, enantiomers or pharmaceutically acceptable salts thereof.

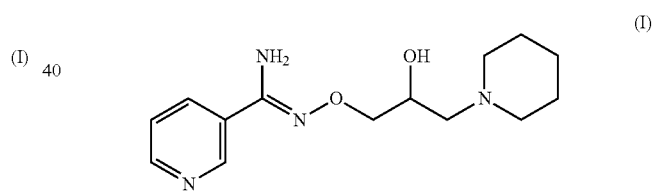

(I)

In a second embodiment, there is provided method to prevent NASH-induced HCC in a subject, comprising administering to a subject affected by NASH the compound of formula I, tautomers, enantiomers or pharmaceutically acceptable salts thereof.

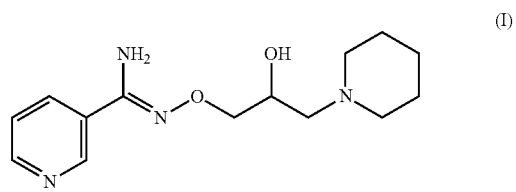 [SMILES: N/C(=N\OCC(O)CN1CCCCC1)c1cccnc1]

(I)

DETAILED DESCRIPTION OF THE INVENTION

As stated above, in a first embodiment, there is provided a method to treat NASH in a subject, comprising administering to such subject the compound of formula I, tautomers, enantiomers or pharmaceutically acceptable salts thereof.

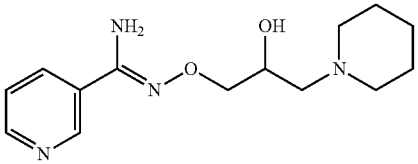

(I)

As stated above, in a second embodiment, there is provided method to prevent NASH-induced HCC in a subject, comprising administering to a subject affected by NASH the compound of formula I, tautomers, enantiomers or pharmaceutically acceptable salts thereof.

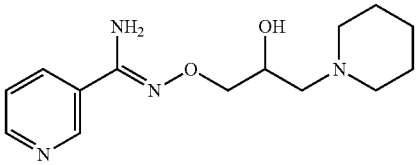

(I)

Previous work has demonstrated that liver inflammation can be reduced in HFD-fed mice by inhibiting the interleukin-6 receptor transsignaling response. (Kraakman et al. 2015)

Treatment with gp130Fc, which is an interleukin-6 receptor transsignaling response inhibitor, can be conveniently mimicked in vivo by using transgenic mice overexpressing the gp130 protein. (Kraakman et al. 2015).

Treatment of HFD-fed MUP-uPA mice that overexpress gp130 with BGP15 leads to an amelioration of the disease.

Accordingly in some embodiments, the methods of the invention further comprise administering to the subject, in combination to BGP15, an inhibitor of the interleukin-6 receptor transsignaling response.

In a specific embodiment, the interleukin-6 receptor transsignaling response inhibitor is gp130Fc or a functional derivative thereof.

Formulation

Compositions provided herein may be in the form of tablets or lozenges formulated in a conventional manner. For example, tablets and capsules for oral administration may contain conventional excipients including, but not limited to, binding agents, fillers, lubricants, disintegrants and wetting agents. Tablets may be coated according to methods well known in the art.

Compositions provided herein may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives.

Compositions provided herein may also be formulated as suppositories, which may contain suppository bases including, but not limited to, cocoa butter or glycerides.

Compositions provided herein may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane.

Compositions provided herein may also be formulated as transdermal formulations comprising aqueous or nonaqueous vehicles including, but not limited to, creams, ointments, lotions, pastes, medicated plaster, patch, or membrane.

Compositions provided herein may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents.

Administration

Administration of the compositions using the method described herein may be orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular.

In some embodiments of the present invention BGP15 is administered in combination with one or more other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

Dosage

The method may comprise administering a therapeutically effective amount of the composition to a patient in need thereof. The therapeutically effective amount required for use in therapy varies with the nature of the condition being treated, the length of time desired to increase hematopoietic stem cells into the bloodstream, and the age/condition of the patient. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more sub-doses per day. Multiple doses may be desired, or required.

The dosage may be at any dosage including, but not limited to, about 0.1 µg/kg, 0.2 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775

μg/kg, 800 μg/kg, 825 μg/kg, 850 μg/kg, 875 μg/kg, 900 μg/kg, 925 μg/kg, 950 μg/kg, 975 μg/kg or 1 mg/kg.

EXAMPLES

The invention is now described by means of non-limiting examples.

Example 1

Treatment of MUP-uPA Mice Undergoing HFD with BGP15

MUP-uPA mice under HFD diet are fed BGP15 containing water in order to achieve BGP15 serum levels ranging between 200 and 400 ng/mL, at which concentration the compound is active. 12 groups of 10 such mice are used in order to determine the efficacy of BGP15 in curing NASH and preventing NASH-induced HCC.

Tumor-free liver samples, blood samples and urine samples are obtained from a cohort at ca. 6 weeks of age to establish baseline measures, and compared with similar samples taken at ca. 24 months of age when NASH and fibrosis, but not tumors, have developed and with samples taken at ca. 32 months of age when tumors have developed. The samples taken are analysed by RNAseq as previously described in Kraakman et al. 2015 and in Umemura et al, 2016. Markers of NASH are serum aspartate transaminase (ALT) levels and serum alanine transaminase (AST) levels, tunel staining for apoptosis, H&E staining for cellular infiltration, Sirius Red staining for fibrosis, Ki67 and K19 staining for cell proliferation and keratin.

As a control, mice fed with a Chow diet, which is a low fat diet, can be used.

Figure 1B:
FIG. 1B portrays the sirus red staining of MUP-uPA mice under HFD diet treated or untreated with BGP15.
Figure 1B:

As set out if FIGS. 1A and 1B, the Sirius red staining of MUP-uPA mice under HFD diet at 24 months of age treated or untreated with BGP15 for 18 weeks, and where in FIG. 1B the darker areas indicate fibrotic areas, treatment with BGP15 dramatically reduces fibrosis.

Figure 2:
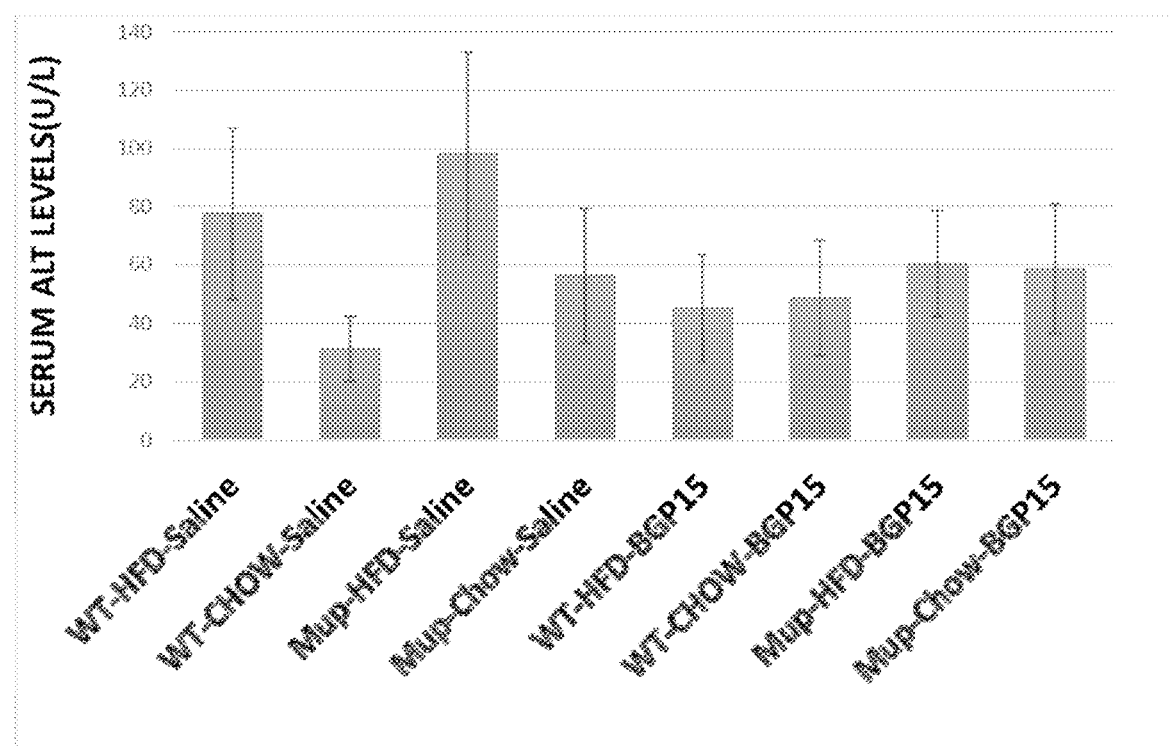
FIG. 2 portrays the ALT levels of wild type (WT) and MUP-uPA mice (Mup) fed with a Chow or an HFD diet, and treated or untreated with BGP15.

As set out in FIG. 2, treatment with BGP15 of HFD fed-mice leads to a reduction of ALT levels.

Example 2

Treatment of MUP-uPA*sgp130 Mice with BGP15

The same procedure described in example 1 above is performed on MUP-uPA mice that have been crossbred with the sgp130 Tg mice described in Kraakman et al. 2015, so as to obtain MUP-uPA*sgp130 mice and determine the efficacy of the combined use of sgp130 and BGP15 in curing NASH and preventing NASH-induced HCC.

BIBLIOGRAPHY

Bardos G et al. Toxicology and Applied Pharmacology (2003), 190(1), 9-16

Clark, J. M., Brancati, F. L. & Diehl, A. M., Am J Gastroenterol 98, 960-967 (2003).
Cohen, J. C., Horton, J. D. & Hobbs, H. H., Science 332, 1519-1523 (2011).
El-Serag, H. B. & Kanwal, F., Hepatology 60, 1767-1775 (2014).
El-Serag, H. B., N Engl J Med 365, 1118-1127 (2011).
Eroglu B et al., Journal of Neurochemistry (2014), 130(5), 626-641
Farkas et al., Biochemical Pharmacology, 2002, 63, 921-932
Gehrig S M et al., Nature (London) 484(7394), 394-398 (2012)
Halmosi et al., Molecular Pharmacology, 2001,59(6), 1497-1505
Kraakman, M. J., et al., Cell Metab 21, 403-416 (2015).
Lazo, M., et al., Am J Epidemiol 178, 38-45 (2013).
Literáti-Nagy B et al., Metabolic Syndrome and Related Disorders (2014), 12(2)
Maurel, M., Samali, A. & Chevet, Cancer Cell 26, 301-303 (2014).
Nagy et al., Toxicology and Applied Pharmacology 243. 96-103 (2010)
Nakagawa, H., et al., Cancer Cell 26, 331-343 (2014).
Sapra, G., et al. Nature communications 5, 5705 (2014).
Starley, B. Q., Calcagno, C. J. & Harrison, S. A., Hepatology 51, 1820-1832 (2010).
Szabados et al., Biochemical Pharmacology. 2000, 59, 937-945
Umemura et al., Cancer Cell. 2016 Jun. 13; 29(6):935-48.
Wu et al., Development, 2015, 142, 681-691

The invention claimed is:
1. A method to prevent non-alcoholic steatohepatitis (NASH)-induced hepatocellular carcinoma in a subject affected by NASH and in need thereof, the method comprising administering to the subject affected by NASH the compound of formula I,

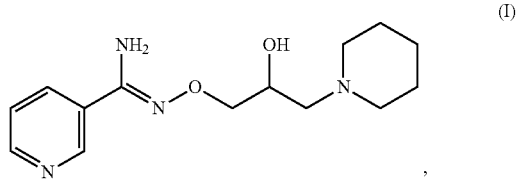 [SMILES: N/C(=N\OCC(O)CN1CCCCC1)c1cccnc1]

(I)

or tautomers, enantiomers or pharmaceutically acceptable salts thereof, wherein the administration prevents NASH-induced hepatocellular carcinoma in the subject.

* * * * *